United States Patent
Eusemann et al.

(10) Patent No.: US 8,654,918 B2
(45) Date of Patent: Feb. 18, 2014

(54) METHOD TO SELECT A VALUE OF A VOLTAGE TO BE SET AT AN X-RAY TUBE, COMPUTER TOMOGRAPHY APPARATUS AND DATA MEDIUM

(75) Inventors: Christian Eusemann, Malvern, PA (US); Berhnard Schmidt, Fuerth (DE)

(73) Assignees: Siemens Medical Solutions USA, Inc., Iselin, NJ (US); Siemens Aktiengesellschaft, Munich (DE)

( * ) Notice: Subject to any disclaimer, the term of this patent is extended or adjusted under 35 U.S.C. 154(b) by 322 days.

(21) Appl. No.: 13/118,803

(22) Filed: May 31, 2011

(65) Prior Publication Data

US 2011/0317806 A1 Dec. 29, 2011

Related U.S. Application Data

(60) Provisional application No. 61/358,227, filed on Jun. 24, 2010.

(51) Int. Cl.
*A61B 6/00* (2006.01)

(52) U.S. Cl.
USPC ............................................. 378/16; 378/111

(58) Field of Classification Search
USPC .......................... 378/8, 16, 65, 101, 108–112
See application file for complete search history.

(56) References Cited

U.S. PATENT DOCUMENTS

| 6,320,929 | B1 | 11/2001 | Von Der Haar |
| 6,501,828 | B1 | 12/2002 | Popescu |
| 2007/0297569 | A1* | 12/2007 | Saunders ...................... 378/108 |
| 2008/0119715 | A1 | 5/2008 | Gonzalez |
| 2010/0040268 | A1 | 2/2010 | Boeing et al. |

FOREIGN PATENT DOCUMENTS

| DE | 19905974 A1 | 7/2000 |
| DE | 19950794 A1 | 6/2001 |
| DE | 102007056481 A1 | 5/2008 |
| DE | 102008037347 A1 | 2/2010 |

* cited by examiner

*Primary Examiner* — Courtney Thomas
(74) *Attorney, Agent, or Firm* — Schiff Hardin, LLP

(57) ABSTRACT

A method is provided to select a value of a voltage to be set at an x-ray tube of a computer tomography for scanning a patient before an acquisition of x-ray projections of a body region of the patient so as to reduce the dose of x-ray radiation to be applied to the patient in the course of the scan. According to the method, the selection of the value of the voltage takes place under consideration of at least one item of information that can be learned from a topogram of the patient and at least one item of information about the patient that can be learned from a patient file of the patient. The invention also encompasses a computer tomography apparatus with a computer for the execution of the method, as well as a data medium on which is stored a computer program that can be executed on a computer device to perform the method.

8 Claims, 1 Drawing Sheet

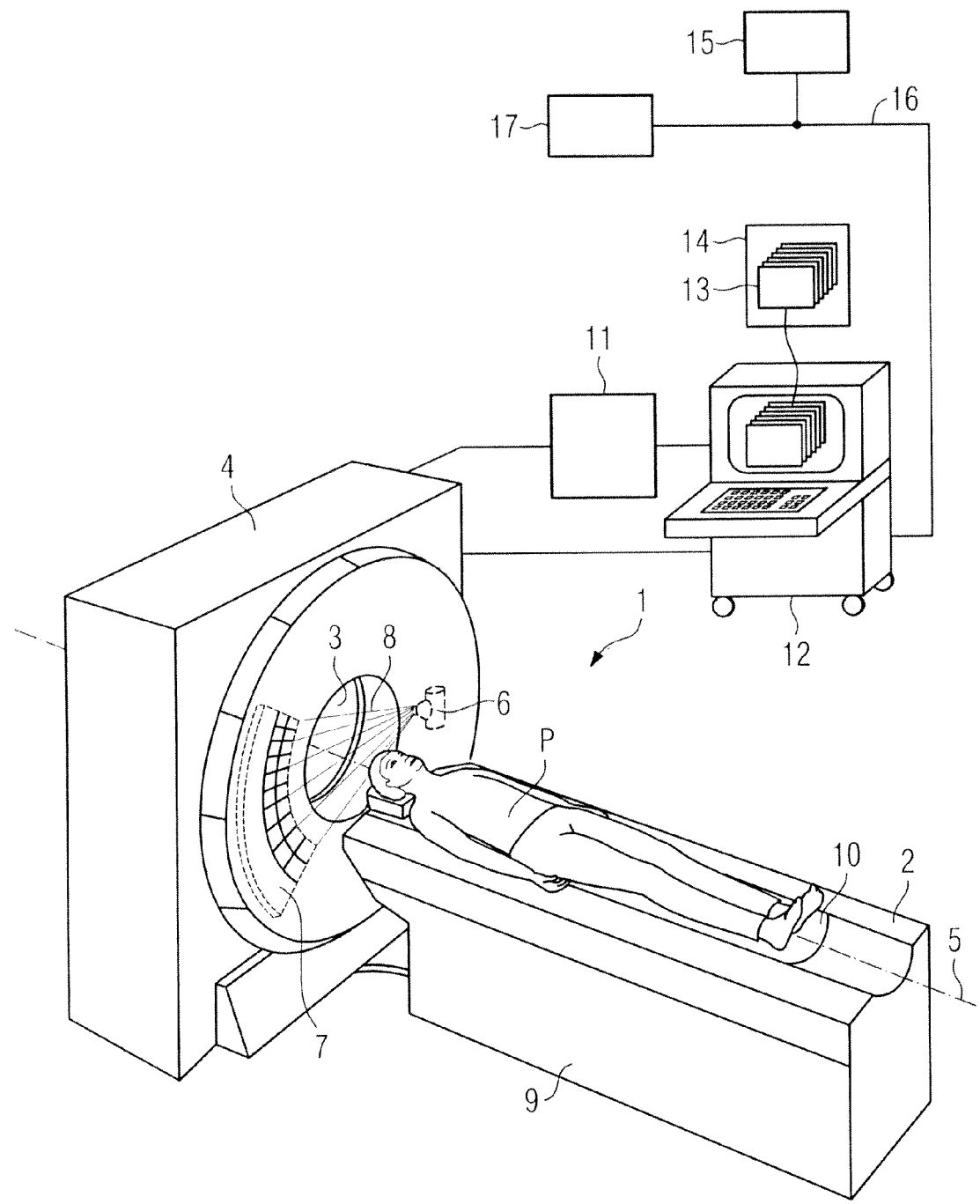

METHOD TO SELECT A VALUE OF A VOLTAGE TO BE SET AT AN X-RAY TUBE, COMPUTER TOMOGRAPHY APPARATUS AND DATA MEDIUM

CROSS-REFERENCE TO RELATED APPLICATION

This application claims the benefit of U.S. Provisional Patent Application Ser. No. 61/358,227, filed Jun. 24, 2010, which is incorporated herein by reference.

BACKGROUND OF THE INVENTION

1. Field of the Invention

The present invention relates generally to a method to select the value of a voltage to be set at an x-ray tube of a computer tomography apparatus for medical imaging of a patient, where the x-ray tube is operated at the selected voltage value for a scan of a region of a body of the patient. The invention also concerns a computer tomography apparatus at whose x-ray tube the voltage is to be set, as well as a data medium that has a program that is executable on a computer device to perform the method.

2. Description of the Related Art

Since the beginning of x-ray computer tomography as a medical imaging technology, it has always been sought to minimize the dose of x-ray radiation applied to a patient during the course of the radiological examination of the patient. There have been various proposals for reducing the radiation dose. For example, German Published Application No. DE 199 05 974 A 1 proposes the use of diaphragms that act in the z-direction (transverse direction to the direction of plane of the x-ray image) that are adjusted during the scan so that essentially only the region of a patient that is used for the reconstruction of the medical images is ever penetrated by an x-ray beam.

In German Published Application No. DE 199 50 794 A1, diaphragms that are dynamically adjustable in the (φ-direction have been proposed that are adjusted depending on the rotation angle during the scanning process such that likewise essentially only the region of a patient that is used for the reconstruction of images is irradiated by an x-ray beam.

Furthermore, a product by the name of "CAREDose" has been developed by Siemens, in which product the tube current of the x-ray tube of the computer tomography apparatus is modulated, depending on the rotation angle and thus on the body cross section of a patient that is to be irradiated, in order to reduce the dose of x-ray radiation to be applied to a patient. For example, the tube current is reduced given x-ray projections in the anterior-posterior direction and is increased given x-ray projections in the lateral direction.

SUMMARY OF THE INVENTION

The present invention provides a method, a computer tomography apparatus and a data medium of the aforementioned type such that the requirements are met to further decrease the dose of x-ray radiation to be applied to a patient in the course of a scan with a computer tomography apparatus. The reduction of the x-ray dose is accomplished by determining the voltage to be supplied to the x-ray tube prior to the acquisition of the x-ray projections. The voltage is set to reduce the dose of x-ray radiation to be applied to the patient in the course of the scan.

According to the invention, the method is utilized to select the value of a voltage to be set at an x-ray tube of a computer tomography apparatus for a scan of a patient—the voltage selection taking place before an acquisition of x-ray projections of a body region of the patient—in order to reduce the dose of x-ray radiation to be applied to the patient in the course of the scan, in which the selection of the value of the voltage takes place under consideration of at least one item of information that can be learned from a generated topogram of the patient and at least one item of information about the patient that can be learned from a patient file of the patient. In a preferred embodiment, the patient file of the patient is an electronic patient file.

The inventors propose to make the selection of a voltage to be set at an x-ray tube of a computer tomography apparatus for a scan of a patient dependent not only on a topogram that is acquired of the patient in advance of the scan, and from which the attenuation of the x-ray radiation by the body of the patient is estimated to select the voltage; rather, it is additionally dependent on at least one individual item of information that can be learned from an (advantageously electronic) patient record. While the information that can be learned from the topogram for the selection of a suitable voltage is accounted for by a purely physical variable, namely the expected attenuation of the x-ray radiation by the body of the patient for example by the body size and proportions of the patient, the medical anamnesis or, respectively, the individual physical constitution of the patient is accounted for by the at least one item of information that can be learned from the patient file. In this way the selection of the voltage to be set can additionally be oriented on the medical anamnesis or, respectively, the individual physical constitution of the patient and—if the circumstances should allow—a lower voltage than that determined from the topogram can be selected and set to reduce the dose of x-ray radiation.

According to one variant of the present method, the selection of the value of the voltage additionally takes place under consideration of the type of examination of the patient, i.e. depending on which tissue, organ or body region is scanned. For example, a lower value for the voltage of the x-ray tube is selected for a CT angiography scan (CTA) than for a scan of the liver in the same patient since the requirements for the image quality, in particular with regard to the level of noise that is acceptable for images of vessels, are lower than for an image of the liver where more detailed image quality is required. Within the context of the present method, a scan also refers to the acquisition of x-ray projections of a body region of a patient from different projection directions, wherein an x-ray system of the computer tomography apparatus (in which the x-ray system comprises at least one x-ray tube and at least one x-ray detector) and the patient normally move relative to one another to scan the body region. Such movement between the x-ray system and the patient need not occur if the x-ray detector has such an extent in the z-direction that the entire body region to be scanned is covered by the x-ray detector or, respectively, that measurement data are acquired with regard to the entire body region to be scanned.

According to one embodiment of the method, the item or items of information that can be learned from the patient file of the patient may include: the number or the frequency of scans that have already been conducted on the patient; an estimation or probability that the patient will develop or contract cancer; information about a previous illness of the patient; information about the health status, a physical property or a tissue property of the patient; information about a contrast agent intolerance of the patient; and/or information about a maximum quantity of contrast agent that may be applied to a patient. If such information about the patient exists in a patient file such that the information can be retrieved (preferably by electronic retrieval of the electronic patient record via a medical facility network or other system), this information can be used in order to possibly correct a value for the voltage of the x-ray tube that is to be set downward to a lower value (relative to the value is obtained on the basis of the topogram alone). The determination of the change in voltage value may be made, for example in a comparison with experimental values of x-ray tube voltages relative to image quality and patient characteristics and knowledge which has been obtained from other patients and, for example, which are assembled in a database or in a look-up table.

According to a further embodiment of the invention, the item or items of information about the health status, a physical property and/or a tissue property of the patient may include an item of information about the health status of the kidneys of the patient, and/or the vein conditions or the diameter of the veins of the patient. Given poor vein conditions of a patient or given relatively small diameters of the veins or the patient, an examination of the veins with a computer tomography may damage the veins of the patient due to the administration of contrast agent if an established flow rate of a contrast agent—i.e. an established injection of contrast agent per time unit into the veins—were to be used for the contrast agent during the examination of the veins of the patient. Depending on the vein conditions or the diameters of the veins, the flow rate of the contrast agent must therefore be decreased for the examination of the patient having the poor vein conditions or the relatively small diameter of the veins. If the health status of the kidneys of the patient might be adversely affected by the administration of larger quantities or the contrast agent, the quantity of contrast agent to be applied to the patient must be decreased in order to avoid additional damage to the kidneys of the patient by the contrast agent. However, the lower flow rate of the contrast agent and/or the decreased quantity of contrast agent administered to the patient has an effect on the achievable contrast in the medical images that result from the acquisition of the x-ray projections. This information would not play any role in the selection of the voltage of the x-ray tube that is to be set solely on the basis of the topogram of the patient. However, if the information about the poor vein conditions, the relatively small diameters of the veins and/or the health status of the kidneys of the patient—and the lower flow rate or quantity of the contrast agent to be used that is connected with these conditions, or, respectively, the lower density of contrast agent in the veins during the examination—is taken into account in the selection of the voltage to be set at the x-ray tube, a lower voltage may be set than the voltage that is determined on the basis only of the topogram. The contrast in reconstructed images of the veins is improved and a smaller dose of x-ray radiation is desirably applied to the patient.

In the same manner, a lower voltage than would be determined on the basis of the topogram of the patient can be switched to for supplying voltage to the x-ray tube if (as was already mentioned in the preceding) a patient has a contrast agent intolerance (which can be learned from the patient file)—for example in the form of information about the patient allergy to a specific contrast agent—or if the medical records contain information that only a specific quantity of contrast agent may be administered to the patient. In these cases as well the quantity of contrast agent to be administered to the patient is normally reduced so that a lower voltage can be switched to for the voltage supplied to the x-ray tube.

According to one variation of the present method, a selection of a value of a mAs value or product to be set in the computer tomography device for the scan of the patient takes place depending on the one or more items of information that can be learned from the patient file of the patient. For example, noise in the acquired measurement data is increased when the voltage applied to the x-ray tube is decreased, for example given the examination of a patient with poor vein conditions. By considering the knowledge of the poor vein conditions and the reduced voltage, the mAs value or product can be increased in order to counteract the increase of the noise. The mAs value for a computer tomography device, which in an example may have a value of 100 mAs, is the product of the tube current to the x-ray tube, for example 200 mA, and the rotation time of the computer tomography device, for example 0.5 s. The selected mAs value and the tube voltage value determine the dose of x-ray radiation applied to the patient.

The patient file from which the information is drawn is preferably electronically stored in a hospital information system (HIS=Hospital Information System) and/or in a radiology information system (RIS=Radiology Information System) and can be retrieved electronically by the computer device that is used to make the determinations of the present method, for example via connection of the computer to a computer network.

The present invention also encompasses an apparatus, including a computer tomography apparatus that has a computer device which is set up (in terms of its programming) to execute one of the methods described in the preceding.

The present invention further encompasses a tangible non-transitory data medium on which is stored a computer program which when executed on a computer having a processor realizes one of the methods described in the preceding, wherein the computer program can be loaded by a computer from the data medium in order to execute one of the methods described herein when the computer program is loaded into the computer. The data medium, for example, can be a CD or another portable storage medium. However, the data medium can also be a server or other computer storage from which the computer program can be retrieved.

BRIEF DESCRIPTION OF THE DRAWINGS

In the single FIGURE is shown a schematic diagram of a computer tomography apparatus for the examination of a patient, including functional block elements depicting elements of the apparatus, according to the principles of the present invention.

DETAILED DESCRIPTION OF THE PREFERRED EMBODIMENTS

An exemplary embodiment of the invention is shown and described. However, in the following (and without limitation of the scope of the invention) a computer tomography apparatus 1 shown in the FIGURE is discussed only insofar as it is deemed necessary to understand the invention to those of ordinary skill in the art.

The computer tomography apparatus 1 shown in the FIGURE has a patient bed 2 to bear or support a patient P to be examined. The x-ray computer tomograph 1 also includes a gantry 4 with a tube detector system borne such that it can rotate around a system axis 5. The tube detector system has an x-ray tube 6 and an x-ray detector unit 7 that are situated opposite one another. In operation, x-ray radiation 8 emanates from the x-ray tube 6 in the direction of the x-ray detector unit 7 and is detected by means of the x-ray detector unit 7.

The patient bed 2 has a bed base or stand 9 on which is disposed a patient bearing plate 10 that is provided to actually bear the patient P. The patient bearing plate 10 can be adjusted relative to the bed base 9 such that the patient bearing plate 10 with the patient P positioned on it can be introduced into the opening 3 of the gantry 4 to acquire x-ray projections of the patient P, for example for a topogram or in a spiral scan. The computational processing of the x-ray programs—for example the generation of a topogram or the reconstruction of a volume data set of a body region of the patient P based on the x-ray projections—takes place with an image computer 11, which is depicted schematically, of the x-ray computer tomograph 1.

The computer tomography apparatus 1 also has a computer 12 with a processor, memory, computer readable storage media, power supply and other computer elements and which executes computer programs stored on the computer storage media to operate and control the computer tomography apparatus 1. The computer 12 can be provided as a separate computer 12 from the computer tomography apparatus or can instead be integrated into the computer tomography apparatus 1. The computer 12 may be connected to a computer network or other computer communication system. The computer storage from which the computer draws programs executed thereon may be entirely within the computer device, stored on a network storage such as a server, or may be stored in distributed storage, such as cloud storage or the like.

In the case of the present exemplary embodiment of the invention, a scan or, respectively, an examination of blood-carrying vessels (in particular veins) of the patient P should take place with the computer tomography apparatus 1, for which contrast agent should be injected into the patient P, for example as prescribed by a doctor as part of a diagnosis or treatment process for the patient.

In preparation of the scan, a topogram of the patient P is initially acquired in a known manner with the computer tomography apparatus 1. The patient's body shape and other body information becomes known.

Furthermore, in the case of the present exemplary embodiment of the invention an acquisition protocol that is suitable for an examination of blood-carrying vessels is selected utilizing the computer 12 from a number of acquisition protocols available for different examinations. Such an acquisition protocol has a plurality of acquisition parameters that are to be set or, respectively, are proposed to be set at the computer tomography apparatus 1 for the respective examination to acquire x-ray projections of the body of the patient. The voltage to be set at the x-ray tube, the table feed, the scan time etc. are among these acquisition parameters, for example.

For the present method, the voltage to be set at the x-ray tube is particularly relevant since the level of the voltage is at least in part determinative of the dose of x-ray radiation applied to the patient P during the scan or, respectively, the examination. In order to meet the requirements to expose the patient with an optimally low dose of x-ray radiation in the course of the scan, a computer program (which is symbolically shown by a block symbol indicted with reference character 13 in the FIGURE) is loaded into the computer 12. The computer program 13 can have been loaded from a portable data medium (for example a CD indicated by reference character 14) or from a server 15 via a network connection 16 into the computer 12 and realizes a method in which the selection or, respectively, the suggestion of the value of the voltage to be set at the x-ray tube 6 for the scan takes place under consideration of at least one item of information that can be learned from the topogram of the patient P and at least one item of information about the patient that can be learned from a patient file of the patient P.

The topogram acquired of the patient is initially evaluated according to the method to obtain information about what attenuation of the x-ray radiation by the body of the patient P is to be expected.

Based on the information about the expected attenuation of the x-ray radiation, the value stemming from the acquisition protocol for the voltage to be set at the x-ray tube 6 of the computer tomography apparatus 1 can be maintained, can be corrected upward or can be corrected downward, wherein a concrete value for the voltage to be set is normally proposed, which concrete value is derived from experimental values based on a plurality of evaluated topograms of other patients. In this way the purely physical circumstances for the selection of the value of the voltage that is to be set are taken into account.

Furthermore, one or more items of information that individually pertain to the patient P and can be learned from a patient file of the patient P are used in the method. The patient file is preferably an electronic patient file that can be or has been stored in a hospital information system (HIS), a radiology information system (RIS) or another electronic information system used in hospitals or clinics and can be retrieved via a network. In the case of the present exemplary embodiment of the invention, the patient file is stored in a hospital information system and can be retrieved via the network 16, which hospital information system is symbolized by the block element labeled with reference character 17.

The electronic patient file normally contains all or at least much of the relevant, known medical information pertaining to the patient, among which belong (among other things) information about the health status of the patient, a physical property or tissue property of the patient; information about a contrast agent intolerance of the patient P; and/or information about a maximum amount of contrast agent that may be applied to a patient. Furthermore, the patient file can contain information about the number or frequency of scans already conducted on the patient P, as well as an estimate or probability that the patient P will develop cancer.

In the case of the present exemplary embodiment, the patient file contains an item of information about a tissue property of the patient P (namely that the patient P has poor vein conditions), and this information is relevant to the intended examination. Poor vein conditions means that the flow rate or, respectively, the injection rate of the contrast agent must be reduced in the examination or, respectively, in the scan in order to not damage the veins of the patient P. For example, the flow rate of the contrast into the patient should be decreased from a conventional 5 ml/s flow rate to 2.5 ml/s flow rate. A reduction in the flow rate of the contrast agent can also be required if, for example, it can be learned from the patient file that the patient P suffers from a contrast agent-induced nephropathy, which is an iatrogenic functional disruption (i.e. a functional disruption that arises due to a medical measure) after an exposure to contrast agent.

In such a case where a reduced flow rate of a contrast agent is used, due to the relatively small volume of contrast agent in the blood-carrying vessels of the patient P a better contrast in reconstructed image data would not appear at a higher tube voltage. For this reason, after consideration of the information about the poor vein conditions of the patient P (which information can be learned from the patient file of the patient P) the tube voltage or, respectively, the voltage to be applied to the x-ray tube 6 can be reduced. For example, the actual level of the voltage to be set can be learned from a database based on experimental values and knowledge. For example, the database can have been developed such that a value for the voltage to be set can be learned with specification of the tube voltage derived from the topogram and the information about the poor vein conditions, which value was used in comparable cases and has delivered good results. Instead of a database, a look-up table can also be used that contains the required information or, respectively, values.

The information that in this case the mAs value* or product (see paragraph above for an explanation) should be increased in order to counteract the image noise by lowering the voltage, and (for example) to achieve a good visualization of the contrast agent (for example iodine), can additionally be learned from the database or, respectively, the look-up table. The value of the mAs value or product can likewise be learned from the database or, respectively, the look-up table or, respectively, be correspondingly proposed based on the database or, respectively, the look-up table, wherein the value—as was previously mentioned—is based on experimental values and experimental knowledge of comparable cases.

The method can be realized such that the determined or, respectively, selected voltage to be set and/or the determined and/or selected mAs value or product to be set are set directly or, respectively, automatically at the computer tomography apparatus 1. However, the determined or, respectively, selected voltage to be set and/or the determined or, respectively, selected mAs value to be set are preferably suggested as settings to the operator of the computer tomography apparatus 1, such that the operator can adopt or reject the automatically determined individual suggestions.

In the case of the present exemplary embodiment of the invention, the voltage to be set and the mAs value to be set were determined on the basis of the topogram and the information about the poor vein conditions of the patient P. In particular with regard to the information that can be learned from a patient file of a patient, additional information about previous illnesses of the patient, about the health status of the patient, etc., can also be used to select the voltage to be set and the mAs product to be set. This information as well as the value for the voltage that is determined using the topogram essentially form a tuple of input variables for the database or, respectively, the look-up table, from which the value for the voltage to be set or, respectively, for the mAs product to be set is selected or, respectively, proposed based on the input values. The suggestion for the mAs product is thereby optional.

Although other modifications and changes may be suggested by those skilled in the art, it is the intention of the inventors to embody within the patent warranted hereon all changes and modifications as reasonably and properly come within the scope of their contribution to the art.

We claim:

1. A method of selecting a value of a voltage to be set for a scan of a patient using an x-ray tube of a computer tomography apparatus before an acquisition of x-ray projections of a body region of the patient, comprising the steps of:
    considering at least one item of information obtained from a topogram of the patient using a programmed computer device;
    considering at least one item of information about the patient obtained from a patient file of the patient using the programmed computer device, wherein the at least one item of information obtained from the patient file of the patient is an item of information selected from the group consisting of: a number of scans that have already been performed on the patient, a frequency of scans that have already been conducted on the patient; an estimation or probability that the patient will develop cancer; an item of information about a prior illness of the patient; an item of information about the health status of the patient; a physical or tissue property of the patient; an item of information about a contrast agent intolerance of the patient; and an item of information about a maximum amount of contrast agent that can be administered to the patient; and
    selecting a value of a voltage to be applied to an x-ray tube of a computer tomography apparatus during a scan of the patient based on said considering of said at least one item of information learned from said topogram and said at least one item of information learned from the patient file so as to reduce a dose of x-ray radiation to be applied to the patient in a course of the scan, said selecting step being performed using the programmed computer device connected to the computer tomography apparatus.

2. A method as claimed in claim 1, further comprising the step of:
    considering a type of examination to be performed on the patient during the scan, said selecting step of the value of the voltage being based on said considering of the examination type, said considering of the type of examination being performed by the programmed computer device.

3. A method as claimed in claim 1, wherein the at least one item of information is an item of information selected from the group consisting of: an item of information about the health status of kidneys of the patient; information on vein conditions of the patient, and information on diameter of veins of the patient.

4. A method as claimed in claim 1, further comprising the step of:
    determining a value of a mAs product to be set for the scan of the patient depending on the at least one item of information obtained from the patient file of the patient, said determining of the value of the mAs product being performed by the programmed computer device.

5. A method as claimed in claim 1, further comprising the step of:
    electronically storing the patient file in at least one of a hospital information system and a radiological information system.

6. A method as claimed in claim 1 or claim 3, further comprising the step of:
    suggesting determined values of a mAs product and/or the determined voltage to be set to an operator for adoption or rejection.

7. A computer tomography apparatus having a computer apparatus, comprising:
    a computer tomography scanner having an x-ray tube and an x-ray sensor;
    a computer connected to operate said computer tomography scanner including said computer being connected to control an operating voltage to said x-ray tube, said computer including a processor operating under the control of a program to execute the following steps:
    considering at least one item of information obtained from a topogram of the patient using a programmed computer device;
    considering at least one item of information about the patient obtained from a patient file of the patient using the programmed computer device, wherein the at least one item of information obtained from the patient file of the patient is an item of information selected from the group consisting of: a number of scans that have already been performed on the patient, a frequency of scans that have already been conducted on the patient; an estimation or probability that the patient will develop cancer; an item of information about a prior illness of the patient;

an item of information about the health status of the patient; a physical or tissue property of the patient; an item of information about a contrast agent intolerance of the patient; and an item of information about a maximum amount of contrast agent that can be administered to the patient; and selecting a value of a voltage to be applied to an x-ray tube of a computer tomography apparatus during a scan of the patient based on said considering of said at least one item of information learned from said topogram and said at least one item of information learned from the patient file so as to reduce a dose of x-ray radiation to be applied to the patient in a course of the scan, said selecting step being performed using the programmed computer device connected to the computer tomography apparatus.

8. A tangible non-transitory data medium on which is stored a computer program, said computer program being executable by a processor of a computer device that is connected to control a computer tomography scanner including being connected to control an operating voltage to said x-ray tube, said program executing the following steps:

considering at least one item of information obtained from a topogram of the patient using a programmed computer device;

considering at least one item of information about the patient obtained from a patient file of the patient using the programmed computer device, wherein the at least one item of information obtained from the patient file of the patient is an item of information selected from the group consisting of: a number of scans that have already been performed on the patient, a frequency of scans that have already been conducted on the patient; an estimation or probability that the patient will develop cancer; an item of information about a prior illness of the patient; an item of information about the health status of the patient; a physical or tissue property of the patient; an item of information about a contrast agent intolerance of the patient; and an item of information about a maximum amount of contrast agent that can be administered to the patient; and selecting a value of a voltage to be applied to an x-ray tube of a computer tomography apparatus during a scan of the patient based on said considering of said at least one item of information learned from said topogram and said at least one item of information learned from the patient file so as to reduce a dose of x-ray radiation to be applied to the patient in a course of the scan, said selecting step being performed using the programmed computer device connected to the computer tomography apparatus.

\* \* \* \* \*

UNITED STATES PATENT AND TRADEMARK OFFICE
CERTIFICATE OF CORRECTION

PATENT NO. : 8,654,918 B2  
APPLICATION NO. : 13/118803  
DATED : February 18, 2014  
INVENTOR(S) : Christian Eusemann et al.

Page 1 of 1

It is certified that error appears in the above-identified patent and that said Letters Patent is hereby corrected as shown below:

Title Page, item [75] inventor change [[Berhnard]] Schmidt to --Bernhard-- Schmidt.

Signed and Sealed this  
Twenty-sixth Day of August, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,654,918 B2  Page 1 of 1
APPLICATION NO. : 13/118803
DATED : February 18, 2014
INVENTOR(S) : Christian Eusemann et al.

It is certified that error appears in the above-identified patent and that said Letters Patent is hereby corrected as shown below:

<u>Title Page,</u>
Item [75], Inventors, "Bernhard" (as corrected to read in the Certificate of Correction issued August 26, 2014) is deleted and patent is returned to its original state with third inventor last name in patent to read --Berhnard--.

Signed and Sealed this
Thirtieth Day of September, 2014

Michelle K. Lee
*Deputy Director of the United States Patent and Trademark Office*